United States Patent [19]

Walker et al.

[11] 4,168,319
[45] Sep. 18, 1979

[54] N-ALKYNYL-2-(SUBSTITUTED PHENOXY) BUTYRAMIDES AND THEIR USE AS MILDEWICIDES

[75] Inventors: Francis H. Walker, Mill Valley; Don R. Baker, Orinda, both of Calif.

[73] Assignee: Stauffer Chemical Company, Westport, Conn.

[21] Appl. No.: 845,514

[22] Filed: Oct. 26, 1977

[51] Int. Cl.² .................. C07C 103/76; A01N 9/20
[52] U.S. Cl. .................. 424/324; 260/559 B
[58] Field of Search .................. 260/559 B; 424/324; 71/118

[56] References Cited

U.S. PATENT DOCUMENTS

| | | | |
|---|---|---|---|
| 3,439,018 | 4/1969 | Brookes et al. | 260/559 B X |
| 3,557,209 | 1/1971 | Richter et al. | 71/118 X |
| 3,677,739 | 7/1972 | Horrom et al. | 71/118 |
| 3,700,732 | 10/1972 | Switchenbank et al. | 71/118 X |
| 3,900,308 | 8/1975 | Poignant et al. | 260/559 B X |
| 3,953,507 | 4/1976 | Baker et al. | 71/118 X |
| 3,971,850 | 7/1976 | Baker et al. | 260/559 B X |
| 4,001,427 | 1/1977 | Baker et al. | 424/304 |
| 4,001,430 | 1/1977 | Baker et al. | 260/559 B X |
| 4,049,423 | 9/1977 | Baker et al. | 260/559 B X |
| 4,049,424 | 9/1977 | Baker et al. | 260/559 B X |
| 4,050,923 | 9/1977 | Baker et al. | 260/559 B X |
| 4,051,184 | 9/1977 | Arneklev et al. | 260/559 B |
| 4,062,977 | 12/1977 | Baker et al. | 260/559 B X |
| 4,070,486 | 1/1978 | Baker et al. | 260/559 B X |
| 4,116,677 | 9/1978 | Walker et al. | 260/559 B X |
| 4,117,166 | 9/1978 | Baker et al. | 260/559 B X |
| 4,119,433 | 10/1978 | Baker et al. | 260/559 B X |

Primary Examiner—Thomas Waltz
Attorney, Agent, or Firm—Michael J. Bradley

[57] ABSTRACT

N-alkynyl-2-(substituted phenoxy) butyramide compounds having the formula

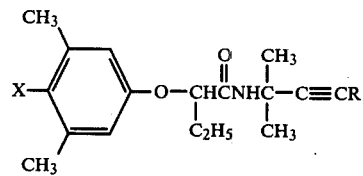

in which X is bromine or methyl and R is hydrogen or methyl, and their use as mildewicides for controlling the growth of mildew are disclosed.

8 Claims, No Drawings

N-ALKYNYL-2-(SUBSTITUTED PHENOXY) BUTYRAMIDES AND THEIR USE AS MILDEWICIDES

BACKGROUND OF THE INVENTION

N-dimethylacetonitrilo-α-(substituted phenoxy) alkyl amides and their use as miticides are disclosed in the prior art in U.S. Pat. No. 4,001,427, which was issued to Don R. Baker and Francis H. Walker on Jan. 4, 1977. These compounds differ substantially from the compounds of the present invention in both their utility and substitution of the phenoxy moiety. Such substitution or change in substitutions would not be expected from the disclosure of applicants' prior patent. A further disclosure of compounds similar to applicants' novel compounds is that of U.S. Pat. No. 3,557,209 to Sydney B. Richter et al. That disclosure again fails, as applicants' own prior disclosure fails, to disclose the novel utility of applicants' compounds or applicants' specific substituted phenoxy moiety.

BRIEF DESCRIPTION OF THE INVENTION

This invention relates to N-alkynyl-2-(substituted phenoxy) butyramides having the formula

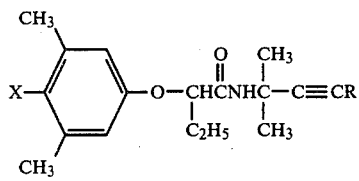

in which X is bromine or methyl and R is hydrogen or methyl, and to their utility as mildewicides for controlling the growth of mildew when used in a mildewicidally effective amount. The compounds of this invention are preferred by conventional reactions using the properly selected starting materials and can be applied by conventional techniques.

DETAILED DESCRIPTION OF THE INVENTION

This invention relates to N-alkynyl-2-(substituted phenoxy) butyramides having the formula

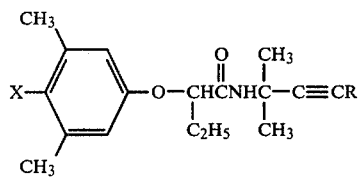

in which X is bromine or methyl and R is hydrogen or methyl, X is preferably bromine and R is preferably methyl and to their utility as mildewicides for controlling the growth of mildew when used in a mildewicidally effective amount.

The term "mildewicide" as used herein refers to a compound which is useful for controlling the growth of fungi, referred to as mildew. Controlling the growth of mildew by applying the compounds described herein can be accomplished by applying a mildewicidally effective amount to the environment in which the growth of mildew fungi is encouraged. The compounds may be applied to any environmental area which supports the growth and development of mildew fungi. By "controlling" is meant the prevention of the growth of the mildew fungi to be controlled.

The novel compounds of this invention may generally be prepared as follows:

1. Preparation of a 3,4,5-trisubstituted phenoxy alkanoic acid.

A properly selected 3,4,5-trisubstituted phenol is reacted wheh a halo-substituted aliphatic acid of the general formula

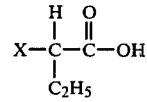

in which X is Cl or Br is the presence of sodium hydroxide at a temperature of from about 40° to about 110° C. to produce the corresponding 2-(3,4,5-trisubstituted)-phenoxy alkanoic acid.

2. Preparation of a 3,4,5-trisubstituted phenoxy alkanoic acid chloride.

The acid prepared in step 1 above is reacted with phosgene at a temperature of from about 40° to about 70° C. in the presence to dimethyl formamide as a catalyst to produce the corresponding 3,4,5-trisubstituted phenoxy alkanoic acid chloride.

3. Preparation of the 3,4,5-trisubstituted phenoxy alkanoic amides of this invention.

The acid chloride prepared in step 2 above is reacted with an amine of the formula

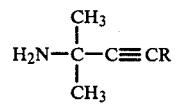

wherein R is hydrogen or methyl in the presence of sodium hydroxide or an organic base such as triethyl amine in a solvent such as methylene chloride at a temperature of from about −15° to about 35° C. to produce the desired amide.

An alternative method of preparation is to react an α-halosubstituted aliphatic acid of the formula

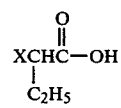

with phosgene and dimethyl formamide catalyst to produce the corresponding acyl chloride of the formula

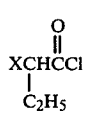

wherein X is Cl or Br, which in turn is reacted with an amine of the formula

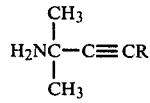

wherein R is hydrogen or methyl in the presence of an organic base such as triethylamine to produce the corresponding α-haloalkylamide.

This amide is reacted with the sodium salt of a phenol of the formula

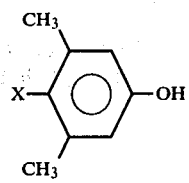

prepared by the reaction of this phenol wherein X is —H or —CH₃ and sodium hydride in tetrahydrofuran as solvent to give the subject amides.

The following examples demonstrate preparation of the novel compounds and utility in controlling mildew fungi.

EXAMPLE I
N-(1,1-DIMETHYLPROPARGYL)-2-(4-BROMO-3,5-DIMETHYLPHENOXY) BUTYRAMIDE a. A solution of 300 grams (1.8 moles) of 2-bromo butyric acid in 350 milliliters of benzene were placed in a 1000 milliliter flask fitted with a gas inlet tube, stirrer, dry ice condenser and thermometer. Ten milliliters of dry dimethylformamide were added to this solution and the mixture was heated to 60° C. 225 grams (2.3 moles) phosgene was added at a moderate rate and when the addition was complete, the dry ice condenser was replaced with a water-cooled condenser and excess HCl and phosgene were removed by purging with argon. The solution was then cooled and the solvent was removed by evaporation at 15 millimeters of mercury pressure to yield 292 grams of an oil (81% yield) identified as 2-bromobutyrylchloride by analysis of nuclear magnetic resonance spectra.

b. 292.4 grams (1.5 moles) of the acyl chloride prepared in step a. above was added to a stirred mixture of 125 grams (1.5 moles) dimethylpropargylamine and 152 grams (1.5 moles) triethylamine in 400 milliliters of methylene chloride held at 10°–15° C. After the addition was complete, the mixture was allowed to come to room temperature and the product was isolated by sequentially washing the mixture with 200 milliliters each of water, diluted HCl and water. The solvent was removed under vacuum after drying over magnesium sulfate. Left was a solid, 197 grams (55% yield), having a melting point of 74°–82° C. The product produced was identified as N-(dimethylpropargyl)-2-bromobutyramide by analysis of nuclear magnetic resonance spectra.

c. 0.8 gram (0.035 mole) of sodium hydride was added to 70 millilters of tetrahydrofuran in a 300 milliliter flask fitted with a stirrer, a thermometer, a reflux condenser and a dropping funnel. The reaction vessel was swept with dry argon throughout the reaction. A solution of 6.0 grams (0.030 mole) 4-bromo-3,5-dimethylphenol in 15 milliliters of tetrahydrofuran was added dropwise to the sodium hydride in tetrahydrofuran with stirring. The resulting reaction mixture was stirred until hydrogen evolution ceased. Next, 7.4 grams (0.030 mole) of N-(1,1-dimethylpropargyl)-2-bromobutyramide prepared in step b. above in 15 milliliters of tetrahydrofuran was added slowly with stirring to this mixture at 25°–30° C. At the completion of the addition, the mixture was heated at reflux for one-half hour and then cooled to room temperature. Then 100 milliliters of water was added under a flow of argon. The resulting mixture was extracted with two 100 milliliter portions of methylene chloride. The extracts were combined and the product was isolated by sequentially washing with 100 milliliters each of water, dilute HCl, 5% of Na₂CO₃ solution and water. The organic phase was dried over magnesium sulfate and the solvent was removed in vacuum to leave 9.9 grams (94% yield) of a solid having a melting point of 104°–106° C. The product was identified as the title compound by analysis of nuclear magnetic resonance spectra.

EXAMPLE II
N-(1,1-DIMETHYL-2'-BUTYRYL)-2-(4-BROMO-3,5-DIMETHYL-PHENOXY) BUTYRAMIDE a. 18 grams (0.09 mole) 4-bromo-3,5-dimethylphenol were mixed with 18 grams (0.11 mole) 2-bromobutyric acid to a 500 milliliter flask equipped with stirring equipment maintained at a temperature of 15° C. 18.4 grams (0.23 mole) of 50% aqueous sodium hydroxide were added to the mixture with rapid stirring. The temperature rose to 45° C. over the course of the addition and was held below 45° C. with a cold bath. After all the sodium hydroxide had been added, cooling was terminated and the mixture was heated at 110° C. for 15 minutes. Then 20 milliliters of water, 50 milliliters of perchloroethylene and 20 milliliters of concentrated HCl were added with stirring, the mixture was heated to 85° C., phase-separated and the organic layer was cooled. The product, which was identified by analysis of nuclear magnetic resonance spectra as 2-(4-bromo-3,5-dimethylphenoxy) butyric acid, separated as a solid which was removed by filtration and air dried to give 21.3 grams (82% yield) of product having a melting point of 78°–85° C.

b. 21.3 grams (0.07 mole) of the acid produced in step a. above were slurried in 50 milliliters of toluene in a 500 milliliter flask fitted with a gas-inlet tube, stirrer, thermometer, and dry ice isopropyl alcohol condenser. 0.2 milliliter of dimethyl formamide was added and the mixture was heated to 60° C. Phosgene was passed into the mixture at a moderate rate until 10.0 grams (0.10 mole) had been added. At the conclusion of the phosgene addition, the dry ice condenser was removed and replaced with a water-cooled condenser. Excess phosgene and hydrogen chloride were removed by purging with argon at 60° C. 21.3 grams (99.6% yield) of the product identified by analysis of nuclear magnetic resonance spectra as 2-(4-bromo-3,5-dimethylphenoxy) butyryl chloride was recovered as an oil from the solution by cooling the solution and removing the solvent under vacuum.

c. 8 grams (0.03 mole) of the acyl chloride produced in step b. above were added dropwise to a 300 milliliter flask containing a stirred solution of 3.9 grams (0.04 mole) 4-amino-4-methyl-2-butyne and 4.0 grams (0.04 mole) triethylamine in 100 milliliters of methylene chloride at 10°–15° C. Some cooling was necessary to maintain the temperature. After all the acyl chloride was added, the mixture was allowed to come to room temperature and the product was isolated by sequentially washing with 100 milliliters each of water, dilute HCl, 5% Na₂CO₃ solution and water. The organic phase was dried over magnesium sulfate and the solvent. was removed in vacuum to leave 6.8 grams (62% yield) of a solid having a melting point of 81.5°–82.5° C. The product was identified as the title compound by analysis of nuclear magnetic resonance spectra.

In the following table, the above two examples are listed together with one additional example which was prepared in a manner analogous to that described above, starting with the appropriate materials. The compounds in the table are representative of those embodied in the present invention. Compound numbers are assigned to each compound and are used through the remainder of the application.

Table I

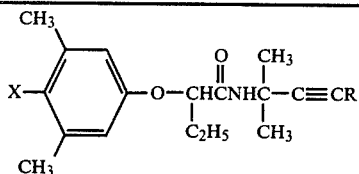

| Compound Number | X | R | Physical Properties |
|---|---|---|---|
| 1 | —Br | —H | m.p. 104°–106° C. |
| 2 | —Br | —CH$_3$ | m.p. 81.5°–82.5° C. |
| 3 | —CH$_3$ | —H | m.p. 100°–102° C. |

FOLIAR FUNGICIDE EVALUATION TESTS

Evaluation for Preventive Action on Bean Powdery Mildew

A candidate chemical is dissolved in an appropriate solvent and diluted with water containing several drops of Tween 20 ®, a polyoxyethylene sorbitan monolaurate wetting agent. Test concentrations, ranging from 1000 parts per million downward, are sprayed to runoff on the primary leaves of Pinto beans (*Phaseolus vulgaris* L.). After the plants are dry, the leaves are dusted with spores of the powdery mildew fungus (*Erysiphe polygoni* De Candolle) and the plants are retained in the greenhouse until the fungal growth appears on the leaf surface. Effectiveness is recorded as the lowest concentration, in parts per million, which will provide 50% reduction in mycelial formation as compared to untreated, inoculated plants. These values are recorded in Table II.

Table II

| | Preventive Action |
|---|---|
| Compound Number | Bean Powdery Mildew |
| 1 | 100 |
| 2 | 25 |
| 3 | 500 |

The compounds of this invention are generally embodied into a form suitable for convenient application. For examples, the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pryophyllite; diatomite; gypsum; clays, propellants, such as dichlorodifluoromethane, etc. If desired, however, the active compounds can be applied directly to feedstuffs, seeds, etc.; upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the presticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

What is claimed:

1. A compostion of matter comprising a mildewicidally effective amount of the compound having the formula

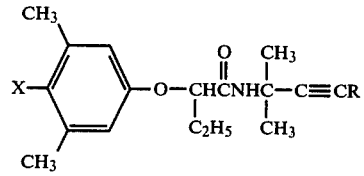

in which X is selected from the group consisting of bromine and methyl and R is selected from the group consisting of hydrogen and methyl and an inert carrier.

2. The composition of claim 1 in which X is bromine and R is hydrogen.

3. The composition of claim 1 in which X is bromine and R is methyl.

4. The composition of claim 1 in which X is methyl and R is hydrogen.

5. A method of controlling the growth of mildew comprising applying to the locus thereof a mildewicidally effective amount of a compound having the formula

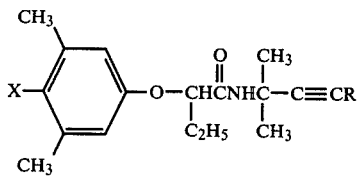

in which X is selected from the group consisting of bromine and methyl and R is selected from the group consisting of hydrogen and methyl.

6. The method of claim 5 in which X is bromine and R is hydrogen.

7. The method of claim 5 in which X is bromine and R is methyl.

8. The method of claim 5 in which X is methyl and R is hydrogen.

* * * * *